United States Patent [19]

Horrobin

[11] Patent Number: 5,604,216
[45] Date of Patent: Feb. 18, 1997

[54] COMPOSITIONS CONTAINING ESTERS OF UNSATURATED FATTY ACIDS

[75] Inventor: David F. Horrobin, Guildford, England

[73] Assignee: Scotia Holdings PLC, England

[21] Appl. No.: 178,553

[22] Filed: Jan. 6, 1994

[30] Foreign Application Priority Data

Jan. 6, 1993 [GB] United Kingdom ............... 9300125

[51] Int. Cl.$^6$ ............... A61K 31/56; C07J 9/00
[52] U.S. Cl. ............... 514/182; 514/169; 552/544
[58] Field of Search ............... 552/544; 514/169, 514/182

[56] References Cited

PUBLICATIONS

Rovesti; "Impieghi Cosmetologici Degli Arachidonati Di Colesterile E Di Ascorbile"; Riv. Ital. Essemze–Profumi, Piante Offic., Aromi–Saponi, Cosmet–Aerosol.; vol. 50, No. 8, 1968, pp. 432–434.

Abdulla et al.; "Differential Resorption Rates of Subcutaneous Implants of [$^3$H]Cholesterol, Varios [$^3$H]Cholesterol esters and [$^3$H]Cholesterol–[1–$^{14}$C]Linolenate; Journal of Atherosclerosis Research"; vol. 9, No. 1, 1969; pp. 81–85.

Sklart et al.; "Induced Circular Dichroism of Incorporated Fluorescent Cholesteryl Esters and Polar Lipids as a Probe of Human Serum Low Density Lipoprotein Structure and Melting"; J. Biol. Chem.; vol. 256, No. 9, 1981; pp. 4286–4292.

Rossner et al.; "Fat Emulsions with Added Free Cholesterol or Fatty Acid Cholesteryl Esters"; Nutr. Metab.; vol. 21, No. 6, 1977; pp. 349–357.

Pownall et al.; "Effect of Saturated and Polyunsaturated Fat Diets on the Composition and Structure of Human Low Density Lipoproteins"; Atherosclerosis; vol. 36, No. 3, 1980; pp. 299–314.

Subbaiah et al.; "Incorporation of Dietary N–3 Fatty Acids Into Molecular Species of Phosphatidyl Choline and Cholesteryl Ester in Normal Human Plasma $^{1-3}$"; Am. J. Clin. Nutr.; vol. 58, 1993; pp. 360–368.

X. Fang et al. "High Performance liquid chromatography . . . " Jour. of Liquid Chromatography, 14(3), 1991, pp. 589–598.

E. Hoving et al. "Separation of cholesterol esters . . . " Jour. of Chromatography, 565 (1991), pp. 103–110.

J. H. Shand et al. "The esterification of cholesterol in the yolk . . . " Lipids, 28(7), 1993, pp. 621–625.

Intl Journal of Clinical Pharmacology Therapy & Toxicology, 1986, 24(12), pp. 668–670.

European Drug Directory, Ed. 2, Paris, SEMP Editions, 1992, p. 1249.

Kagawa et al, *Chemical Abstracts*, vol. 102, No. 23, abstract #203048u, 1985, p. 523.

Glick et al, *Chemical Abstracts*, vol. 107, No. 3, abstract #21426m, 1987, p. 438.

*Primary Examiner*—Marianne M. Cintins
*Assistant Examiner*—William R. A. Jarvis
*Attorney, Agent, or Firm*—Nixon & Vanderhye

[57] ABSTRACT

Pharmaceutical and nutritional compositions are disclosed containing, in association with a suitable diluent or carrier, at least 10% by weight of a cholesterol fatty acid ester where the fatty acid is gamma-linolenic acid, dihomo-gamma-linolenic acid, adrenic acid, the 22:5 n-6 acid, stearidonic acid, the 20:4 n-3 acid, eicosapentaenoic acid, docosahexaenoic acid, the 22:5 n-3 acid or columbinic acid. Novel cholesterol columbinic acid esters are described.

13 Claims, No Drawings

COMPOSITIONS CONTAINING ESTERS OF UNSATURATED FATTY ACIDS

FIELD OF INVENTION

The invention relates to compositions containing esters of unsaturated fatty acids.

BACKGROUND

Fatty acids of specific types are of considerable interest both for the maintenance of healthy tissue and in the treatment of various diseases. Some fatty acids are of interest in themselves, some because they give rise to particular metabolites such as prostaglandins or other oxygenated derivatives, and some for both reasons. Among them are the essential fatty acids (EFAs) not made by the body and therefore constituting essential nutrients. Among the EFAs of particular interest for both reasons are gamma-linolenic acid (GLA), dihomogammalinolenic acid (DGLA) and eicosapentaenoic acid (EPA). DGLA is an important component of cell membranes and is also the precursor of prostaglandin $E_1$ ($PGE_1$); $PGE_1$ has many desirable effects being an antithrombotic, anti-inflammatory, vasodilator, immunomodulating and cholesterol lowering agent. GLA is an immediate precursor of DGLA and is rapidly converted to DGLA within the body. EPA is also a component of cell membranes and is a precursor of $PGE_3$ which has actions similar to those of $PGE_1$. A further fatty acid which is of particular interest as a component of cell membranes is docosahexaenoic acid (DHA).

The conversation pathways of the main series of EFAs in the body are as follows:

TABLE 1

| n-6 | n-3 |
|---|---|
| 18:2 delta-9,12 (linoleic acid) | 18:3 delta-9,12,15 (alpha-linolenic acid) |
| | \| |
| | delta-6 desaturase |
| | ↓ |
| 18:3 delta-6,9,12 (gamma-linolenic acid) | 18:4 delta-6,9,12,15 (stearidonic acid) |
| | \| |
| | elongation |
| | ↓ |
| 20:3 delta-8,11,14 (dihomo-gamma-linolenic acid) | 20:4 delta-8,11,14,17 |
| | \| |
| | delta-5 desaturase |
| | ↓ |
| 20:4 delta-5,8,11,14 (arachidonic acid) | 20:5 delta-5,8,11,14,17 ('eicosapentaenoic acid') |
| | \| |
| | elongation |
| | ↓ |
| 22:4 delta-7,10,13,16 (adrenic acid) | 22:5 delta-7,10,13,16,19 |
| | \| |
| | delta-5 desaturase |
| | ↓ |
| 22:5 delta-4,7,10,13,16 | 22:6 delta-4,7,10,13,16,19 ('docosahexaenoic acid') |

The above pathways are not normally reversible nor, in man, are n-3 and n-6 series acids inter-convertible.

The acids, which in nature are of the all-cis configuration, are systematically named as derivatives of the corresponding octadecanoic, eicosanoic or docosanoic acids, eg. delta-9,12-octadecadienoic acid or delta-4,7,10,13,16,19-docosahexaenoic acid, but numerical designations such as, correspondingly, 18:2 n-6 or 22:6 n-3 are convenient. Initials, for example, EPA for the 20:5 n-3 acid (eicosapentaenoic acid) or DHA for the 22:6 n-3 acid (docosahexaenoic acid), are also used but do not serve when n-3 and n-6 acids of the same chain length and degree of unsaturation exist as for example with the 22:5 acids. Trivial names in more or less common use in the n-6 series are as shown. Of the n-3 series only 18:3 n-3 has a commonly used trivial name, alpha-linolenic acid, though the name stearidonic acid is coming into use for the 18:4 n-3 acid and the names eicosapentaenoic acid and docosahexanenoic acid as such are also used. The alpha isomer of linolenic acid was characterised earlier than gamma-linolenic acid and reference in the literature simply to linolenic acid, especially in the earlier literature, is to the alpha-acid.

Discussion

The value of cholesterol esters of fatty acids has not been previously recognised because of the idea that cholesterol is harmful and likely to precipitate disease of the coronary and peripheral arteries. It has been forgotten by many that cholesterol is an essential constituent of the body and is absolutely required for the normal composition of cell membranes. Cholesterol esters form a major part of the LDL (low density lipoprotein) particles which circulate in the blood. LDL particles are taken up into cells which have specific receptors known as LDL receptors on their surfaces. LDL receptors occur on many types of cells but are expressed in very large numbers on many cancer cells. As is well known, LDL receptors are also found on cells associated with the arteries. Cholesterol esters of the present fatty acids are therefore an effective way of delivering these fatty acids to cells which have LDL receptors. They are a particularly effective way of delivering fatty acids to cancerous cells and atherosclerotic tissues.

In general, fatty acids have therapeutic value in a range of different disorders. As discussed herein and in other patents by the present inventor, these fatty acids are of value in the treatment of cancer. The acids, particularly gamma-linolenic acid, dihomo-gamma-linolenic acid, arachidonic acid, eicosapentaenoic acid and docosahexaenoic acid, have desirable actions on the cardiovascular system and are of value in the treatment of coronary and peripheral arterial disease. The same fatty acids may be produced to a restricted degree in patients with diabetes and can therefore be of value in the treatment of diabetic complications such as neuropathy, retinopathy and cardiovascular disease. Some of the acids, particularly gamma-linolenic acid, dihomo-gamma-linolenic acid, and eicosapentaenoic acid have anti-inflammatory effects and can be used in disorders in which inflammation is an important constituent such as rheumatoid arthritis, osteoarthritis, eczema, inflammatory bowel disease, psoriasis and the autoimmune group of diseases. These fatty acids are also particularly important in brain function and of value in the management of serious cerebral and psychiatric disorders such as schizophrenia, alcoholism, and dementias including Alzheimer's disease and multi-infarct dementia. These possible uses of fatty acids are however examples of those that are known and the present invention is not meant to be applied simply to the use of the fatty acids for these particular disorders. The significance in the context lies in the method of delivering these fatty acids by administering them in the form of cholesterol esters for the treatment of any of the above and of any other disease.

A further aspect of the value of the cholesterol esters in the above context and more widely is wholly new. We have found that the cholesteryl esters are unusually stable and resistant to oxidation, much more so than the fatty acids themselves, or their salts or triglyceride or other forms. This is well illustrated by their performance when incorporated into creams or ointments for regular topical use. In the past we have made various formulations of EFAs for topical use and have used free fatty acids, salts and triglycerides. Unless protected by an effective antioxidant, such creams or ointments allow rapid oxidation of the fatty acid component. In contrast, creams and ointments made up containing cholesteryl salts behave completely differently. For example, we made creams containing 5% and 10% cholesteryl-GLA without any added antioxidant to evaluate their performance. In contrast to what usually happens, even when these creams are in containers which are opened every day and so exposed to fresh oxygen repeatedly, they remain pure white for periods of months. This indicates that the choleseteryl esters of the EFAs are exceptionally resistant to oxidation. As far as we are aware this has never been reported previously and provides a clear reason for preparing cholesteryl-esters of the EFAs in all the types of formulation listed elsewhere in this patent specification. There is an especial reason for using the cholesteryl esters in formulations of pharmaceuticals or other materials for skin care, cosmetics or the treatment of skin diseases. Topical preparations in these situations are exposed to high levels of oxygen as they are spread thinly on the skin and a stable form of the EFAs is therefore of particular value in this situation.

The Invention

From the above, the invention has a number of aspects.

In one aspect there are the cholesterol esters of the n-6 and n-3 essential fatty acids, parinaric acid and columbinic acid, so far as they are new compounds.

In another aspect, there are the above esters, new in themselves or not, in their hiterto unsuggested and valuable use in pharmaceutical skin and nutritional compositions.

In a further aspect there is the use of the esters for the preparation of medicaments for treatment of conditions as set out above, and corresponding methods of treatment as such, being conditions in which it is required to transport the fatty acids into the intracellular compartment and in particular cancer and atheroslerosis (the binding to the LDL receptor and transport into the cell by this route is then the means by which the generally desirable principle of getting the fatty acids into the cells is achieved) or conditions in which a stable form of the fatty acid, not readily oxidised, is requisite. Such conditions are most clearly those requiring application of topical compositions, but stability of the fatty acids is of general importance and their use in a form not requiring association with a separate antioxidant is at great value.

This last aspect is not in fact limited to the fatty acids and purposes set out above and in a further aspect the invention thus lies in the use, for the preparation of unsaturated and particularly polyunsaturated fatty acid compositions resistant to atmospheric oxidation of fatty acid cholesterol esters; or a method of making such fatty acids resistant to atmospheric oxidation wherein the fatty acids are esterified with cholesterol.

Synthesis of the Esters

The cholesterol esters are specific molecules which contain one molecule of cholesterol esterified with one molecule of the desired fatty acid. They may be prepared by the reaction of cholesterol with the fatty acid concerned, the desired fatty acid in the reaction mixture suitably constituting more than 20% of the fatty acid present, preferably more than 40%, very preferably more than 70% and ideally more than 90%. The fatty acids may be prepared by methods known to those skilled in the art either by chemical synthesis or by extraction and purification from natural sources. Esterification procedures are known to those skilled in the art.

As examples of methods by which cholesterol esters of fatty acids may be made, the following are given. First, prepare the chloride derivative of the fatty acid by reacting the pure fatty acid with thionyl chloride. Then prepare the cholesterol fatty acid ester by mixing the fatty acid chloride with cholesterol in the presence of dichloromethane and pyridine. The products of the reaction are the fatty acid cholesterol ester and hydrochloric acid. Another method of preparation is to mix cholesterol with p-toluene sulphonic acid hydrate in toluene and to heat under reflux with the fatty acid concerned. The water from the reaction forms an azeotropic mixture with the toluene and this mixture is separated off and the remaining toluene removed in vacuo. The brown oily residue can then be subjected to dry column chromatography. Initial elution with hexane removes a fore-running impurity, and then elution with 5% diethyl ether gives the required ester from which the solvent can be removed. The esters of the fatty acids specified are slightly yellow viscous oils. Other methods of preparation may be used by those skilled in the art.

Cholesterol esters of other unsaturated fatty acids may be prepared in the same way. Parinaric acid (18:4 n-3; 9 cis, 11 trans, 13 trans, 15 cis) is one of particular interest because of its strong anti-cancer actions. Columbinic acid (18:3 n-6; 6, 9 cis, 13 trans) is also of interest because it can perform the membrane-related actions of essential fatty acids without being converted to eicosanoids.

The following are particular examples, covering synthesis of the following cholesteryl esters (1):

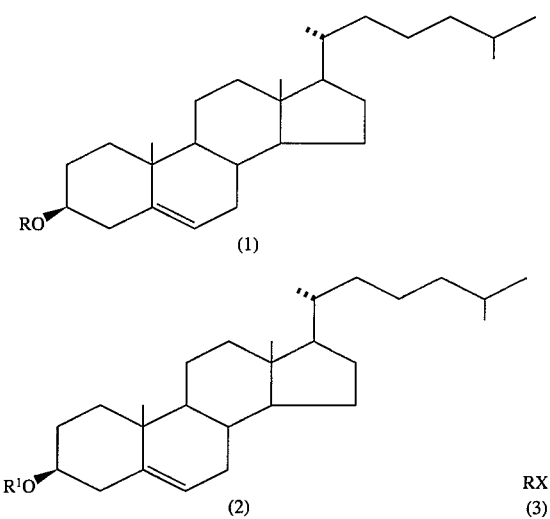

Compounds of type (1) where R is $R^2C=O$ and $R^2$ is an alkyl chain corresponding to the n-6 and n-3 essential fatty acids, parimaric acid and columbinic acid may be synthesised in the following ways:

(a) By reaction of cholesterol (compounds of type (2), $R^1$=H) with fatty acids of type (3) wherein R is as above and X=H, in the presence of a catalytic amount of a suitable mineral acid e.g. p-toluene sulphonic acid, in an inert solvent which will azetrope water i.e. toluene, xylene at temperatures between 100° C. to 180° C.

(b) By reaction of cholesterol (compounds of type (2), $R^1$=H) with fatty acids of type (3) wherein R is as above and X=H, in the presence of condensing agent, e.g. dicyclohexyl carbodiimide, a strong non-nucleophilic base. e.g. 4-dimethylaminopyridine and in a suitable insert solvent e.g. dichloromethane at 10°–40° C.

(c) By reaction of cholesterol (compounds of type (2), $R^1$=H) with fatty acid chlorides or bromides of type (3) wherein R is as above and X=Cl or Br, in the presence of a suitable base, e.g. pyridine ad in an insert solvent e.g. dichloromethane at 0°–50° C.

(d) By reaction of cholesterol acetate (compounds of type (2), $R^1$=$CH_3CO$) with fatty acid esters of the lower alcohols of type (3) wherein R is as above and X=$X^1$=$O(CH_2)_nCH_3$(n=0–2) in the presence of a catalytic amount of an alkoxide of type $MX^1$ wherein $X^1$ is herein before defined and M is an alkali metal, e.g. sodium or potassium, under reduced pressure and at a temperature of 80°–120° C.

The preferred compounds are compounds of type (1) where:

| | | |
|---|---|---|
| 1A) | R = (z,z,z) Octadeca-6,9,12-trienoyl. | $C_{45}H_{74}O_2$ |
| 1B) | R = (z,z,z,z) Eicosa-5,8,11,14-tetraenoyl | $C_{47}H_{76}O_2$ |
| 1C) | R = (z,z,z,z,z) Eicosa-5,8,11,14,17-pentaenoyl | $C_{47}H_{74}O_2$ |
| 1D) | R = (z,z,z,z,z,z) Docosa-4,7,10,13,16,19-hexaenoyl | $C_{49}H_{76}O_2$ |

The starting compounds of types (2) and (3) are readily available commercially, and are defined as follows:

| | | |
|---|---|---|
| 2A) | $R^1$ = H | |
| 2B) | $R^1$ = $CH_3CO$ | |
| 3AH) | R = (z,z,z) Octadeca-6,9,12-trienoyl. | X = H |
| 3ACl) | R = (z,z,z) Octadeca-6,9,12-trienoyl. | X = Cl |
| 3BMe) | R = (z,z,z,z) Eicosa-5,8,11,14-tetraenoyl. | X = Me |
| 3CMe) | R = (z,z,z,z,z) Eicosa-5,8,11,14,17-pentaenoyl. | X = Me |
| 3DH) | R = (z,z,z,z,z,z) Docosa-4,7,10,13,16,19-hexaenoyl. | X = H |

EXAMPLE 1.

The Preparation of Cholesteryl (z,z,z) octadeca-6,9,12-trienoate. (1A): A solution of 556 parts of (z,z,z) octadeca-6,9,12-trienoic acid (3AH), 773 parts of cholesterol (2A) and 20 parts of p-toluene sulphonic acid monohydrate in 2500 parts of toluene was stirred heated under reflux and under nitrogen with a Dean and Stark head to remove the water formed. After approx. 5 hours water production ceased and the mixture was cooled. The solvent was removed in vacuo, the residual brown oil dissolved in hexane (2000 parts) and the resulting solution washed with water and dried ($Na_2SO_4$). This solution was subjected to medium pressure column chromatography (Column: 6000 parts Matrex silica, pore size 60 A, particle size 35–70 µm. Solvent: Hexane). The requisite tractions were collected and the solvent was removed in vacuo to give cholesteryl (z,z,z) octadeca-6,9, 12-trienoate, (1A) as a pale yellow non-distillable oil.

EXAMPLE 2.

The Preparation of Cholesteryl (z,z,z) octadeca-6,9,12-trienoate (1A): A solution of 335 parts cholesterol (2A) and 70 parts of dry pyridine in 1500 parts of dichloromethane was cooled to 5°–10° C. and was stirred under nitrogen whilst 257 parts of (z,z,z) octadeca-6,9,12-trienoyl chloride (3ACl) was added dropwise over 30 min. The mixture was allowed to stir at room temperature for 20 hours. After removal of the solvent in vacuo, hexane (1000 parts) was added and the resulting mixture was extracted with aqueous 2M hydrochloric acid (300 parts) and water (3×300 parts). The organic layer was dried ($Na_2SO_4$) and the solvent removed in vacuo to give a brown oil. This oil was subjected to dry column chromatography (Column: 1000 parts of Matrex silica, pore size 60 A, particle size 35–70 µm. Solvent: Hexane). The requisite fractions were collected and the solvent removed in vacuo to give cholesteryl (z,z,z) octadeca-6,9,12-trienoate, (1A) as a pale yellow non-distillable oil.

EXAMPLE 3.

The Preparation of Cholesteryl (z,z,z,z,z) eicosa-5,8,11,14,17-pentaenoate, (1C): A mixture of 330 parts of cholesteryl acetate (2B), 270 parts of methyl (z,z,z,z,z) eicosa-5,8,11,14,17-pentaenoate (3CMe) and 5 parts sodium ethylate was stirred and heated under vacuum (110° C./0.01 mmHg) for 4 hours. After cooling the residue was subjected to medium pressure column chromatography (Column: 10000 parts of Matrex silica, pore size 60 A, particle size 35–70 µm. Solvent: 1% diethyl ether in hexane). The requisite fractions were collected and evaporated in vacuo to give cholesteryl (z,z,z,z,z) eicosa-5,8,11,14,17-pentaenoate, (1C) as a non-distillable colourless oil.

By replacing the method (z,z,z,z,z) eicosa-5,8,11,14,17-pentaenoate with the equivalent amount of methyl (z,z,z,z) eicosa-5,8,11,14-tetraenoate (3BMe), there was obtained Cholesteryl (z,z,z,z) eicosa-5,8,11,14-tetraenoate, (1B) as a colourless non-distillable oil.

EXAMPLE 4.

The Preparation of Cholesteryl (z,z,z,z,z,z)-4,7,10,13,16, 19-hexaenoate, (1D): To a solution of 118 parts of cholesterol (2A), 69 parts of dicyclohexyl carbodiimide and 41 parts of 4-dimethylaminopyridine in dichloromethane (2000 parts) under nitrogen was added 100 parts of (z,z,z,z,z,z) docosa-4,7,10,13,16,19-hexaenoic acid (3DH). The mixture was stirred for 2 hours at room temperature and then filtered to remove the precipitated dicyclohexyl urea. The filtrate was evaporated at room temperature in vacuo and the residue was subjected to dry column chromatography (Column: 10000 parts of Matrex silica, pore size 60 A, particle size 35–70 µm. Solvent: 9:1 Hexane: Diethyl ether). The requisite fractions were collected and evaporated in vacuo to give cholesteryl (z,z,z,z,z,z) docosa-4,7,10,13,16,19-hexaenoate, (1D) as a colourless non-distillable oil.

Administration

The cholesterol esters may be administered orally, topically, parenterally (subcutaneously, intramuscularly, intravenously), enterally, rectally, vaginally or by another other appropriate route. They may be made up into tablets, hard or soft gel capsules, pastilles, emulsions, enteral or parenteral formulae, foams, ointments, creams, lotions, suppositories, pessaries or any other appropriate form known to those skilled in the art. They may be made up into pharmaceutical dosage forms, or into foods which have a specific medical or health-related purpose, and also skin care preparations. The cholesterol esters for use in these various formulations may contain more than 20% by weight of the specific fatty acid ester desired related to total fatty acid, preferably more than 40%, very preferably more than 70% and ideally more than 90%.

The doses for oral or parenteral or topical administration may suitably be prepared so as to deliver from 1 mg to 100 g, preferably from 100 mg to 20 g and very preferably from 500 mg to 10 g of the cholesterol ester per day. When prepared for topical administration or in enteral or parenteral formulations or food they may be made in formulae containing from 0.01% to 60% by weight of the final formulation, preferably from 0.1% to 30% by weight, and very preferably from 1% to 10% by weight.

The preparations may be used to maintain health or to treat any disease likely to respond to the fatty acid, particularly to treat cancers, where the cells frequently have large numbers of LDL receptors and are likely to incorporate substantial amounts of the fatty acid, as a result of its administration in cholesterol ester form.

The invention is further illustrated by the following formulation Examples.

Examples of Formulations

1. Soft gelatin capsules containing 100 mg, 250 mg, 500 mg or 750 mg of cholesterol-GLA.

2. Hard gelatin capsules containing 100 mg, 200 mg, 500 mg or 750 mg of cholesterol-GLA.

3. Pastilles or other oral dosage forms including whips, foams, chocolate, or enteral or parenteral foods containing 0.1% to 50% by weight of cholesterol-GLA.

4. Topical skin care or pharmaceutical preparations such as creams, ointments or lotions or other formulations containing 0.1% to 50% by weight of cholesterol-GLA.

5. Tablets containing 100 mg, 250 mg, 500 mg or 750 mg cholesterol-GLA.

6. Emulsions for enteral or parenteral administration in which cholesterol-GLA is incorporated at a level of 0.1% to 20% by weight.

7–12. Formulations as in 1–6 but containing cholesterol-DGLA.

13–18. Formulations as in 1–6 but containing cholesterol-EPA.

19–24. Formulations as in 1–6 but containing docosahexaenoic acid, parinaric acid or columbinic acid.

25–30. Formulations as in 1–6 containing arachidonic acid, adrenic acid or stearidonic acid.

31–36. Formulations as in 1–6 but containing linoleic acid or alpha-linolenic acid.

37–72. Formulations as in 1–36 in which the desired cholesterol ester makes up more than 20%, preferably more than 40%, very preferably more than 70% and ideally more than 90% of all the cholesterol esters present in the preparation.

I claim:

1. A pharmaceutical or nutritional composition comprising at least 10% by weight of a cholesterol fatty acid ester, wherein the fatty acid is selected from the group consisting of gamma-linolenic acid, dihomo-gamma-linolenic acid, adrenic acid, the 22:5 n-6 acid, stearidonic acid, the 20:4 n-3 acid, eicosapentaenoic acid, docosahexaenoic acid, the 22:5 n-3 acid and columbinic acid, in association with a suitable diluent or carrier.

2. A skin care composition comprising at least 10% by weight of a cholesterol fatty acid ester, wherein the fatty acid is selected from the group consisting of gamma-linolenic acid, dihomo-gamma-linolenic acid, adrenic acid, the 22:5 n-6 acid, stearidonic acid, the 20:4 n-3 acid, eicosapentaenoic acid, docosahexaenoic acid, the 22:5 n-3 acid and columbinic acid, in association with a suitable diluent or carrier.

3. The composition of claim 1 or claim 2 containing more than 20% by weight of the fatty acid ester.

4. The composition according to claim 3 containing more than 40% by weight of the fatty acid ester.

5. The composition according to claim 4 containing more than 70% by weight of the fatty acid ester.

6. The composition according to claim 5 containing more than 90% by weight of the fatty acid ester.

7. The composition of claim 1 or claim 2 wherein the composition is in a form to provide a daily dose of from 1 mg to 100 g of the fatty acid ester.

8. The composition according to claim 7 wherein the daily dose provided is from 100 mg to 20 g.

9. The composition according to claim 8 wherein the daily dose provided is from 500 mg to 10 g.

10. The composition of claim 1 or claim 2 comprising from up to 60% of the ester.

11. The composition according to claim 10 comprising up to 30% by weight of the ester.

12. The composition according to claim 11 comprising 10% by weight of the ester.

13. A cholesterol fatty acid ester, wherein the fatty acid is columbinic acid.

* * * * *